United States Patent [19]

Reese et al.

[11] Patent Number: 4,726,238
[45] Date of Patent: Feb. 23, 1988

[54] MICRO SAMPLING VALVE FOR HIGH PRESSURE AND TEMPERATURE SAMPLES

[75] Inventors: Norman A. Reese, Whittier; Jack Berroteran, Orange, both of Calif.

[73] Assignee: Chevron Research Corporation, San Francisco, Calif.

[21] Appl. No.: 929,927

[22] Filed: Nov. 12, 1986

Related U.S. Application Data

[63] Continuation of Ser. No. 806,070, Dec. 6, 1985, abandoned.

[51] Int. Cl.$^4$ .............................................. G01N 35/00
[52] U.S. Cl. ................................ 73/864.83; 73/864.84
[58] Field of Search ........... 73/863.41, 863.51, 863.54, 73/863.61, 863.71, 863.72, 863.73, 863.81, 863.85, 864.31, 864.51, 864.81, 864.63, 864.64, 864.83, 864.84, 864.85, 23.1

[56] References Cited

U.S. PATENT DOCUMENTS

| | | | |
|---|---|---|---|
| 3,100,984 | 8/1963 | Martin | 73/863.73 |
| 3,583,233 | 6/1971 | Jacoby et al. | 73/864.83 |
| 3,643,511 | 2/1972 | Warncke et al. | 73/864.83 |
| 4,425,810 | 1/1984 | Simon et al. | 73/863.11 |

FOREIGN PATENT DOCUMENTS 0805106 2/1981 U.S.S.R. ........................... 73/864.83

OTHER PUBLICATIONS

"Portable Chromatographic Sample Valve", Jayco Technical Products Company.
"A New System for Obtaining Vapor and Liquid Sample Analyses to Facilitate the Study of Multicomponent Mixtures at Elevated Pressure" by Yarborough et al; Pan American Petroleum Corp.; Tulsa, Okl., Chemical Eng. Progress Symposium Series.
"Vapor Liquid Equilibria Up to 100 MpA:A New Apparatus" by D. Legret et al., AICHE Journal (vol. 27, No. 2) Mar. 1981.

*Primary Examiner*—Stewart J. Levy
*Assistant Examiner*—Robert R. Raevis
*Attorney, Agent, or Firm*—S. R. La Paglia; E. J. Keeling; E. A. Schaal

[57] ABSTRACT

The present invention provides an apparatus and method for trapping and injecting a fluid sample (liquid or gas) at high temperature and pressure without any sample loss. Here, a sample is flowed into an aperture in the valve body and then into a sample chamber. The sample chamber is mounted in a slidable stem and once the sample is in the sample chamber, the stem is moved to a position to seal off the sample. Once the sample is trapped, the valve is moved to a chromatograph (while maintaining the sample at pressure and temperature), flushed with a carrier gas, and the stem is moved to open the sample chamber to the gas. This flushes the sample and moves it to the chromatograph.

3 Claims, 4 Drawing Figures

U.S. Patent
Feb. 23, 1988
4,726,238
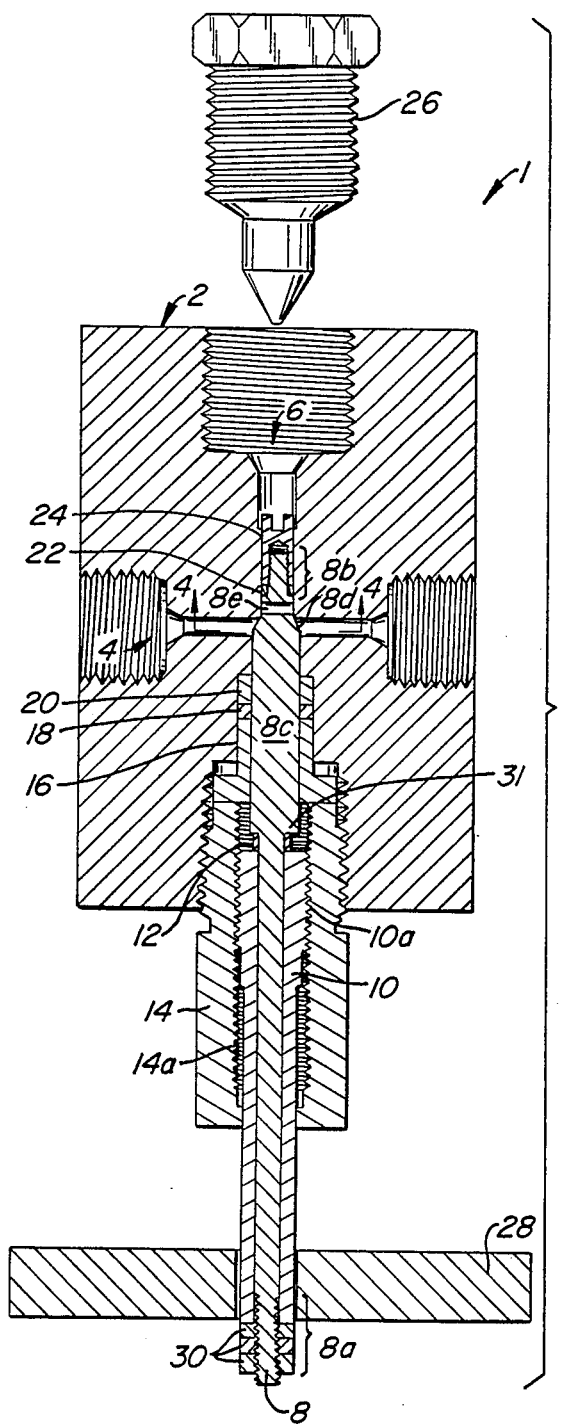
FIG._1.
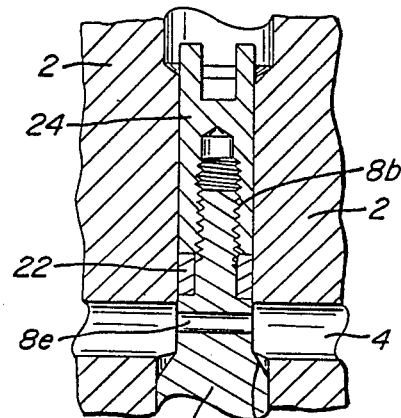
FIG._2.
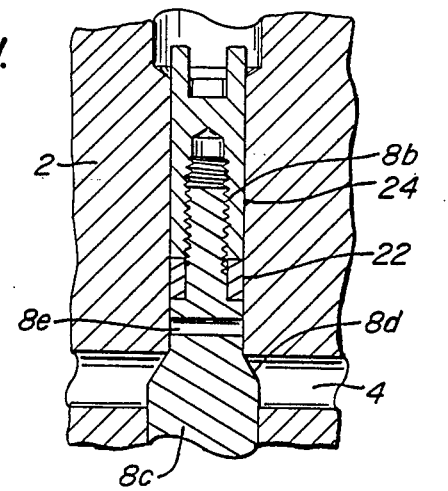
FIG._3.
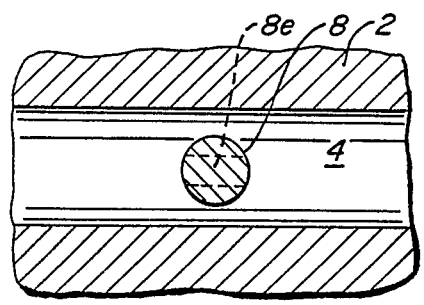
FIG._4.

MICRO SAMPLING VALVE FOR HIGH PRESSURE AND TEMPERATURE SAMPLES

This is a continuation of application Ser. No. 806,070, filed Dec. 6, 1985, and now abandoned.

BACKGROUND OF THE INVENTION

1. Field of the Invention

This invention generally relates to fluid sampling. Here, the present invention provides a method and apparatus for trapping and injecting a fluid sample (liquid or gas) at high pressure and temperature, into a chromatograph with no sample loss.

2. Background Information

In petroleum reservoirs, liquids and gases exist under high-pressure, high-temperature conditions. To observe the properties of these fluids in the laboratory, all samples must remain in this condition to truly reflect their natural state. Here, a petroleum sample is taken from the reservoir and brought to the surface where it is subjected to a lower temperature and pressure. However, once in the laboratory, the sample is returned to a single phase by placing it in a device to repressurize and reheat it. (See U.S. Pat. No. 4,425,810 to Simon et al). In the high-pressure visual cell of U.S. Pat. No. 4,425,810, measurements are made either visually or by other optical means. Thereafter, hydrocarbon analyses must be made (usually in a gas chromatograph) so that a sample must be removed from the high-pressure, temperature environment to one of low pressure and temperature.

Some techniques which analyze samples from a high-pressure cell simply bleed off the sample into the low-pressure environment of the gas chromatograph. However, this causes problems. The single-phase mixture of hydrocarbons may separate into two phases, (i.e., gas and oil) which would affect the analyses. Or, there may simply be time delays. For example, bleeding off a sample requires cleaning up the entire cell, putting a new sample in the cell, and repressurizing the system, which itself can take up to one day of labor.

For these reasons, it is important to take a micro sample and keep it under the same high-pressure, high-temperature conditions that exist in the cell. When these conditions are maintained, the hydrocarbon mixture will not separate into two phases. Furthermore, due to the size of the micro sample, the addition of another sample in the cell would be unnecessary.

Several valves have been designed that take micro samples of a fluid at a high temperature and pressure. See Lyman Yarborough and John Vogel, "A New System for Obtaining Vapor and Liquid Sample Analyses to Facilitate the Study of Multi-Component Mixtures at Elevated Pressures", 81 Chem. Eng. Prog. Symp. Series-Phase Equilibria and Related Properties 1 (1967); and D. Legret et al, "Vapor Liquid Equilibria Up to 100 MPa: A New Apparatus", 27 AIChE Jour. 203 (March, 1981). Both show valves that will take such a sample. However, the valve of Yarborough et al has a problem in that the sample is trapped in a cavity that is out of the flow path that leads to the chromatograph. Since the micro sample is placed in a "dead space", all of the components of the hydrocarbon sample may not be properly analyzed because they may not be flushed through the valve. The Legret valve suffers from the same problem as the sample is trapped in an area that is not directly in the flow path to the chromatograph which means that a portion of the sample may be left behind and not analyzed. Furthermore, the Legret valve is used to sample hydrocarbons that have a high boiling point and it consequently does not have the same versatility as the present invention.

The present invention seeks to eliminate the problems encountered in analyzing a high-pressure, high-temperature fluid sample and also to overcome the problems inherent in the Yarborough and Legret valves. To overcome those disadvantages, the present invention brings the micro-sample into the carrier gas rather than having the sample expand into the carrier gas from a dead space. Due to this procedure, the present invention may trap, for analysis, oils that are highly volatile where the other valves may not.

SUMMARY OF THE INVENTION

The micro sampling valve is an apparatus for trapping and injecting a fluid sample (liquid or gas) at high pressure and temperature into a chromatograph without any sample loss. The valve comprises a body that has a flow passage and apertures adapted for the sampling apparatus. The sampling apparatus comprises a sampling stem and some associated hardware to seal the sampling stem from fluid leaks and, to move the stem in a lengthwise direction. A sampling chamber is located in the sampling stem so that, when the valve is open, the chamber is directly in the path of the fluid to be sampled. When the sampling stem is moved axially, the sample is trapped in the chamber (by the close fit to the valve body and the seals), which maintains the integrity of the sample. The valve is then removed from the sampled atmosphere, cleaned of residual fluids and connected to the injection loop of a chromatograph. The carrier gas of the chromatograph is flushed through the sample entry line and the valve is then opened to the carrier gas flow thus carrying the total sample into the chromatograph.

BRIEF DESCRIPTION OF THE DRAWINGS

FIG. 1 is a longitudinal cross-sectional view through the micro sampling valve;

FIG. 2 is an enlarged longitudinal cross-sectional view through the sampling area of the valve showing the sampling chamber open to the flow path;

FIG. 3 is an enlarged longitudinal cross-sectional view of the sampling area of the valve in which the sampling chamber has been sealed off from the flow path; and FIG. 4 is a cross-sectional view through the width of the sampling valve in the area of the fluid aperture.

DETAILED DESCRIPTION OF THE INVENTION

The micro sampling valve provides a method and apparatus for trapping and injecting a fluid sample (liquid or gas) at a high pressure and temperature into a chromatograph with no sample loss. Referring now to FIG. 1, the micro sampling valve 1 is shown. The valve 1 has a valve body 2 with a sample flow aperture 4 and an aperture for receiving the means for sampling (sampling means aperture) 6. The sampling means aperture 6 contains the sampling components. These components include a non-rotating sampling stem 8 and a stem sleeve 10 adapted to fit over the sampling stem 8.

There are threads 14a on the gland nut 14 and corresponding threads 10a on the stem sleeve 10 to move the non-rotating sampling stem 8 in and out. A handle 28 may be fixed to the stem sleeve 10 to rotate the stem sleeve 10 which bears against a shoulder 31 on the sample stem and pushes or pulls the non-rotating sampling stem 8 in or out. End bearing washers and nuts 30 are fit to the non-rotating sampling stem 8. A bearing washer 12 is fit between the stem sleeve 10 and the shoulder 31 on the non-rotating sampling stem 8 so that the two stems may be fit together properly and to ensure that the non-rotating stem 8 does not rotate. The non-rotating sampling stem 8 has two threaded ends, 8a and 8b, an enlarged portion 8c, a tapered portion 8d, and sample chamber 8e opposite the enlarged portion 8c. A gland nut 14 is fit over the stem sleeve 10 and the non-rotating sampling stem 8 and fits this assembly into the valve body 2. Both the gland nut 14 and the stem sleeve 10 are threaded to match each other at 14a and 10a, respectively. The gland nut 14 also compresses a packing 18 between a seal follower 16 and a seal stopper (or packing gland) 20 to establish a fluid-tight high-pressure seal against the gland nut 14 and around the non-rotating sampling stem 8. The seal follower 16 and the seal stopper 20 confine the packing 18 and keeps it from extruding under pressure. A seal ring 22 and a packing nut 24 are fit on the non-rotating stem on the side of the sample aperture opposite the enlarged portion 8c from the sample chamber 8e. A plug 26 may be fit into the valve body 2 to protect the aperture 6 from dirt, etc.

The valve body 2, the gland nut 14, the seal follower 16, and the seal stopper 20 are all constructed of 316 stainless steel. The non-rotating sampling stem 8 and the packing nut 24 are made of 17-4 PH with a hardness of H900. The packing 18 is made of a partially compressible substance—possibly plastic, Teflon (which is a trademark for polytetrafluoroethylene), or Buna "N" (one of a number of German rubber substitutes prepared by the polymerization of butadiene). The sealing 22 is also made of a compressible substance, such as Teflon, but needs a material to keep it from becoming too fluid under the high-pressure and temperature conditions. For this application, glass-filled Teflon may be appropriate.

FIGS. 2, 3, and 4 show enlarged cross-sectional portions of the device in FIG. 1 in the area of the sampling chamber 8e. FIG. 2 shows the sampling chamber 8e in the open position and FIG. 3 shows the sampling chamber 8e in the closed position. FIG. 4 shows a widthwise cross section through the non-rotating sampling stem 10 in the area of the aperture 4.

The micro sampling valve 1 operates in the following manner. The valve 1 may be attached to a high-pressure visual cell (see U.S. Pat. No. 4,425,810) which contains a hydrocarbon sample either in the gas or the liquid state. The connection between the valve 1 and the cell is made at the sample flow aperture 4. For sampling, the valve 1 is oriented with the non-rotating sampling stem 8 in the open position as enlarged in FIG. 2. An outside pressure source is then operably connected to the high-pressure visual cell to push the sample out of the cell and into the sample flow aperture 4. This is done slowly so that problems due to pressure changes are minimized. The hydrocarbon sample, that exists in either the gas or the liquid state, is now pushed into the sample flow aperture 4 and occupies the sample chamber 8e in the sampling stem 8. No sample is allowed up the walls of the sampling stem 8 because of the closeness of fit between the sampling stem 8 and the valve body 2 as well as the associated sealing members. When a sample occupies the space in the sampling chamber 8e, the sampling stem 8 is slidably moved in the direction of the plug 26 so that the sample chamber 8e is enclosed by the valve body 2 and the sampling stem 8.

The handle 28 is rotated which rotates the stem sleeve 10. The stem sleeve threads 10a and the gland nut threads 14a push the non-rotating sampling stem 8 forward without allowing the non-rotating sampling stem 8 to rotate. (To further prevent rotation, the non-rotating stem 8 could even be "keyed" with lateral slots or it could be made with an oval cross section.) Here, there is no leakage of the sample past the walls of the sampling stem 8 because of a knife-edge seal between the tapered portion 8d of the sampling stem 8 and the shoulder of the valve body 2 in the area of the sample flow aperture 4. Another seal is created on the other side of the sample chamber 8e by the seal ring 22 and the packing nut 24. With the sampling stem 8 in this position, the sample chamber 8e is closed off and the sample flow has to go around the sample stem 8 (the diameter of the sample stem 8 is less than the diameter of the sample flow aperture 4, see FIG. 4). After the sample has been trapped in the sample chamber 8e, the remaining bulk of the sample itself is pushed back into the high-pressure visual cell by a reverse action on the pressurizing source. This returns substantially all of the sample to the visual cell with the exception of the few microliters that are now in the sample chamber 8e.

When the sample is trapped in this position, it is still charged with the high pressure and temperature that existed when it first flowed into the sample chamber 8e. The micro sampling valve 1 may now be: disengaged from the visual cell; flushed with solvent to remove any residual oil and mercury from aperture 4; dried; and then connected to a gas chromatograph at the sample flow aperture 4. An outlet for a carrier gas may be attached to one side of the sample flow aperture 4 and an input line to the gas chromatograph may be connected to the other side of the sample flow aperture 4. When all connections have been properly made, the carrier gas is flowed through the sample flow aperture 4 past the sampling stem 8. When the gas chromatograph is ready, the sampling stem 8 is slidably moved back to its open position so that the sample chamber 8e is left open to the sample flow aperture 4. At this point, the carrier gas sweeps all of the sample out of the sample chamber 8e and into the sample flow aperture 4 where it is then carried to the gas chromatograph. This process allows for very efficient sweep of the entire sample out of the sample chamber 8e and into the chromatograph.

The procedure outlined above is very efficient in taking a very small sample from a pressurized sample at temperature and transferring it to an analyzing device without any loss of the sample itself. The valve 1 performs this task while still maintaining the sample under pressure. This eliminates problems due to condensation, phase separation, and other lengthy mechanical preparations.

Since many modifications and variations of the present invention are possible within the spirit of this disclosure, it is intended that the embodiments disclosed are only illustrative and not restrictive. For that reason, reference is made to the following claims rather than to the specific description to indicate the scope of this invention.

What is claimed is:

1. A valve for trapping and injecting a fluid sample at a high pressure and temperature, comprising:

(I) a valve body having an aperture for sample flow and an aperture to receive a sampling means (sampling means aperture), both apertures intersect one another and are 90° to each other along their lengthwise axes;

(II) a non-rotating sampling stem located in the sampling means aperture, said sampling stem having:
(a) two threaded ends;
(b) an enlarged portion adjacent the sample flow aperture;
(c) a tapered portion on the non-rotating sampling stem, so that when the stem is slidably moved along its lengthwise axis, the tapered portion forms a knife-edge seal in conjunction with the valve body at the point that the sample flow aperture and the sampling aperture meet;
(d) a sample chamber placed completely through the non-rotating sampling stem adjacent the tapered portion and opposite said enlarged portion at substantially 90° to the lengthwise axis of the non-rotating sampling stem, within and parallel to, the sample flow aperture;
(e) a shoulder on said enlarged portion of the non-rotating sample stem;
(f) the non-rotating sampling stem being adapted to move along its lengthwise axis;

(III) a means to hold the non-rotating sampling stem in place and seal the space between the valve body and the non-rotating sampling stem, comprising:
(a) a stem sleeve adapted to fit over said non-rotating sampling stem bears against said shoulder, the stem sleeve used for moving the non-rotating sample stem chamber in and out of the sample flow aperture;
(b) a bearing washer located between the stem sleeve and the shoulder on the non-rotating sampling stem, the bearing washer being used to keep the non-rotating sampling stem from rotating while rotating the stem sleeve;
(c) a packing having an aperture through which the non-rotating sampling stem is inserted on one side of the sample flow aperture, the packing is used to seal the pressure in the valve and keep the sample from leaking past the non-rotating sampling stem;
(d) a packing gland having an aperture through which the non-rotating sampling stem is inserted, the packing gland is fit between said packing and the sample flow aperture, the packing gland is used to keep the packing from extruding;
(e) a seal follower having an aperture through which the non-rotating sampling stem is inserted and a bearing surface which fits against the packing, the seal follower is located on the other side of the packing from the packing gland and is used to confine the packing and keep the packing from extruding under pressure;
(f) a gland nut adapted to fit over the stem sleeve behind the seal follower, the gland nut being used to compress the packing between the seal follower and the packing gland to seal the non-rotating sampling stem and hold a pressurized seal;

(IV) sealing means fit on the non-rotating sampling stem on the side of the sample flow aperture opposite said enlarged portion comprising:
(a) a seal ring having an aperture through which the sampling stem is inserted;
(b) a packing nut to fit on the end of the sampling stem, against the seal ring, the packing nut having a slot for tightening onto the sampling stem to compress the seal ring to provide a high-pressure seal; and
(c) a sealing plug adapted to fit into the valve body to protect the aperture from small object contamination.

2. The valve as described in claim 1 where the sample chamber is a cylinder, of a volume, running through the non-rotating sampling stem at 90° to the lengthwise axis of the non-rotating sampling stem and parallel to the direction of flow of the sample which operates to capture a sample by moving from the flow stream to a position in which the open ends are sealed by the valve body.

3. A valve for trapping and injecting a fluid sample at high pressure and temperature, comprising:
a valve body;
a sample flow aperture and a sampling means aperture within the valve body;
a sampling stem located within the sampling means aperture, the sampling stem intersecting the sample flow aperture;
a sampling chamber transversely located within the sampling stem in the area of the sample flow aperture, so that a sample may flow into said sampling chamber;
means for exposing the sampling chamber to a high-pressure, high-temperature sample;
means for trapping the sample within the sampling chamber;
means for establishing a high-pressure seal around the sample aperture after the sample has been trapped further comprising:
(a) a seal ring having a seal ring aperture through which the sampling stem is inserted;
(b) a packing nut to fit on the end of the sampling stem, against the seal ring, the packing nut having a slot for tightening onto the sampling stem to compress the seal ring to provide a high-pressure seal; and
(c) a sealing plug adapted to fit into the valve body to protect the sampling means aperture from small object contamination; and
means for exposing the sample, in the sampling chamber, to a carrier fluid to sweep the sample out of the sampling chamber to be analyzed.

* * * * *